United States Patent
Hall et al.

(10) Patent No.: US 10,209,264 B2
(45) Date of Patent: *Feb. 19, 2019

(54) METHOD OF DETECTING DRUG TAGGANTS IN BIOLOGICAL SAMPLES TO ASSESS DRUG DECAY

(71) Applicants: David R. Hall, Provo, UT (US); Dan Allen, Springville, UT (US); Conrad Rosenbrock, Provo, UT (US); Daniel Hendricks, Provo, UT (US); Andrew Nguyen, Provo, UT (US); Steven J. M. Butala, Provo, UT (US); Travis Niederhauser, Mapleton, UT (US); Terrece Pearman, Draper, UT (US); Joe Fox, Spanish Fork, UT (US)

(72) Inventors: David R. Hall, Provo, UT (US); Dan Allen, Springville, UT (US); Conrad Rosenbrock, Provo, UT (US); Daniel Hendricks, Provo, UT (US); Andrew Nguyen, Provo, UT (US); Steven J. M. Butala, Provo, UT (US); Travis Niederhauser, Mapleton, UT (US); Terrece Pearman, Draper, UT (US); Joe Fox, Spanish Fork, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/496,407

(22) Filed: Apr. 25, 2017

(65) Prior Publication Data

US 2018/0306826 A1  Oct. 25, 2018

(51) Int. Cl.

| | |
|---|---|
| *G01N 33/94* | (2006.01) |
| *G01N 33/493* | (2006.01) |
| *G01N 33/15* | (2006.01) |
| *A61B 5/15* | (2006.01) |
| *A61G 10/00* | (2006.01) |
| *A47K 17/00* | (2006.01) |
| *A61B 10/00* | (2006.01) |
| *G01N 33/58* | (2006.01) |

(52) U.S. Cl.
CPC .............. *G01N 33/94* (2013.01); *A47K 17/00* (2013.01); *A61B 5/15* (2013.01); *A61B 10/007* (2013.01); *A61B 10/0038* (2013.01); *A61B 10/0051* (2013.01); *G01N 33/15* (2013.01); *G01N 33/493* (2013.01); *G01N 33/58* (2013.01); *A61B 2010/0061* (2013.01); *A61B 2010/0077* (2013.01); *A61B 2010/0087* (2013.01); *G01N 2458/00* (2013.01)

(58) Field of Classification Search
None
See application file for complete search history.

(56) References Cited

U.S. PATENT DOCUMENTS

| | | | | |
|---|---|---|---|---|
| 6,025,200 A | * | 2/2000 | Kaish .................. | G01N 21/643 422/83 |
| 2002/0106045 A1 | * | 8/2002 | Hata ...................... | G01N 23/22 376/156 |
| 2014/0065171 A1 | * | 3/2014 | Geierstanger .......... | C07K 16/00 424/179.1 |
| 2014/0309505 A1 | * | 10/2014 | Euliano ................ | A61B 5/4833 600/302 |

OTHER PUBLICATIONS

Sheraz, M.A. et al. 2014. Photo, thermal and chemical degradation of riboflavin. Beilstein Journal of Organic Chemistry 10: 1999-2012. specif. pp. 1999, 2002, 2009.*
Whitworth, C.W. et al. 1973. Stability of aspirin in liquid and semisolid bases III: effect of citric and tartaric acids on decomposition in a polyethylene glycol base. Journal of Pharmaceutical Sciences 62(10): 1721-1722. specif. pp. 1721, 1722.*
Saenz, A. 2009. Smart Toilets. Datasheet [online]. Copyright 2018. Singularity Education Group [retrieved on May 7, 2018]. Retrieved from the Internet: <URL: https://singularityhub.com/2009/05/12/smart-toilets-doctors-in-your-bathroom/#sm.0001y4o5it122uesaygr8rrwc5kyf> pp. 1-3.*

* cited by examiner

*Primary Examiner* — Renee Claytor
*Assistant Examiner* — Sharon M. Papciak

(57) ABSTRACT

We disclose a method of using taggants to assess how and to what extent a drug in a drug composition that a user has consumed has decayed in response to storage conditions and time. The taggants may decay in response to environmental conditions which cause different drugs to lose their efficacy. These environmental conditions may include light, temperature, oxidation, moisture, and age. The taggants may be detected in biological samples, including urine and feces. By identifying the taggants, the drug composition and other information relating to the drug may be identified. Additionally, quantification of the different taggants may be used to determine whether the drug in the drug composition has been exposed to environmental conditions which may reduce its efficacy.

14 Claims, 8 Drawing Sheets

| Name | Structure |
|---|---|
| Polyethylene Glycol | 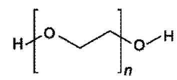 |
| Ethylene Vinyl Acetate | 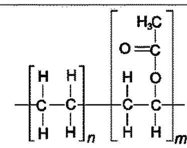 |
| Providone | 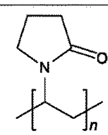 |
| Copovidone | 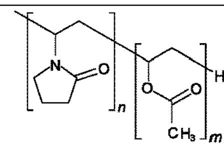 |
| Propylparaben | 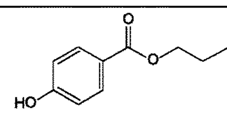 |
| Methylparaben | 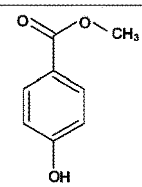 |
| Sucralose | 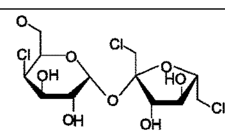 |
| Acesulfame K | 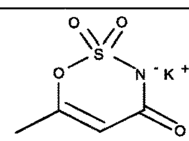 |
| Sorbitol | 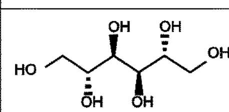 |
| Mannitol | 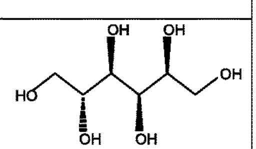 |
| Xylitol | 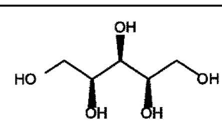 |

FIG. 4

| Name | Structure |
|---|---|
| Steviol Glycoside | 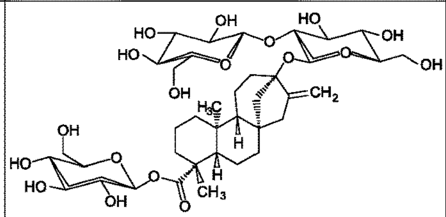 |
| Riboflavin | 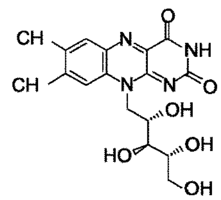 |
| Oleic Acid | 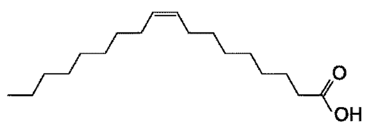 |
| Tartaric Acid | 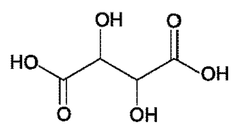 |
| 1, 8-eucalyptol | 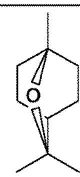 |
| Trans-anethole | 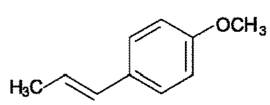 |
| Limonene-2D | 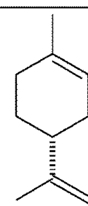 |
| Linalool | 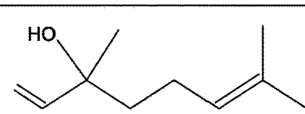 |
| Citronellol | 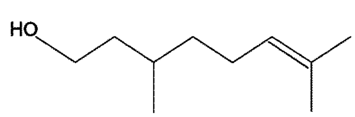 |

| Name | AVG MW (g/mol) | Example MW Range (g/mol) |
|---|---|---|
| PEG 400 | 400 | 380-420 |
| PEG 600 | 600 | 570-630 |
| PEG 800 | 800 | 720-880 |
| PEG 1000 | 1000 | 950-1050 |
| PEG 1500 | 1500 | 1300-1650 |
| PEG 2000 | 2000 | 1900-2200 |

FIG. 7

METHOD OF DETECTING DRUG TAGGANTS IN BIOLOGICAL SAMPLES TO ASSESS DRUG DECAY

BACKGROUND

Field of the Invention

This disclosure relates to methods of tracking and identifying the age or amount of degradation of pharmaceuticals after consumption using drug taggants.

Background of the Invention

Consumption of drugs which have reduced efficacy or are unsafe due to aging or prolonged exposure to certain environmental conditions creates a health risk. Methods for managing this problem include printing an expiration date on the drug packaging and applying aging strips that change color over time to drug packaging. However, these methods simply predict the status of a consumed drug but do not actually detect the consumption of outdated or degraded drug.

An additional problem is abuse of prescription drugs. If a patient does not consume all the prescribed medication a person other than the patient may consume that medication. This may occur when the patient shares unused drug with another or illegally sells the drug. The drug may not be effective when the other person receives it due to improper storage or age.

In these and other scenarios it is not only beneficial to be able to identify the consumed drug, but also to determine whether the drug has experienced significant degradation from age, extreme temperature, light, or other environmental conditions.

A method is needed to tag drug compositions in a way that both identifies the drug composition and determines whether it has aged or decayed by analyzing a biological sample collected from a user who has consumed the tagged drug composition.

BRIEF SUMMARY OF THE INVENTION

We disclose a method of using one or more taggants which may be added to drug compositions to assess decay of a drug in the drug composition due to environmental conditions or age. The taggants may be detectable in a biological sample, including urine or feces. The taggants may have one or more decay characteristics which may include light sensitivity, temperature sensitivity, sensitivity to moisture, and decay due to chemical degradation over time. The drug composition may include taggants that possess qualitatively or kinetically the same decay characteristics as the drug in the drug composition. The drug composition may also include taggants that possess different decay characteristics relative to the drug in the drug composition. Alternatively, multiple taggants, some with the same and some with different decay characteristics may be included.

The taggants may be present in the drug composition in defined ratios. The ratio may provide at least some of the uniqueness of the taggant associated with the drug composition. The taggants, including their relative ratios, may indicate drug composition manufacturer, drug, drug composition, manufacturing batch, dispensing pharmacy, prescribing healthcare provider, healthcare provider's institution, and prescribed user.

The taggants may be detectable in biological samples collected from a user who has consumed the drug composition with the taggants. The biological sample may include urine, feces, or other biological materials.

Examples of chemicals which may be used as taggants include polyethylene glycol, copovidone, povidone, propylparaben, methyl paraben, acesulfame potassium, mannitol, sorbitol, xylitol, steviol glucuronide, sucralose, oleic acid, trans-anethole, 1,8-eucalyptol, limonene-2D, linalool, citronellol, riboflavin, tartaric acid, and salts of tartaric acid.

BRIEF DESCRIPTION OF THE DRAWINGS

FIG. 4 is a table showing the names and chemical structures of examples of relatively stable molecules which may be used in taggants according to the disclosure.

FIG. 7 is a table showing variations of polyethylene glycol molecules which may be used as taggants according to the disclosure.

DETAILED DESCRIPTION OF THE INVENTION

Definitions

Figure 1A:
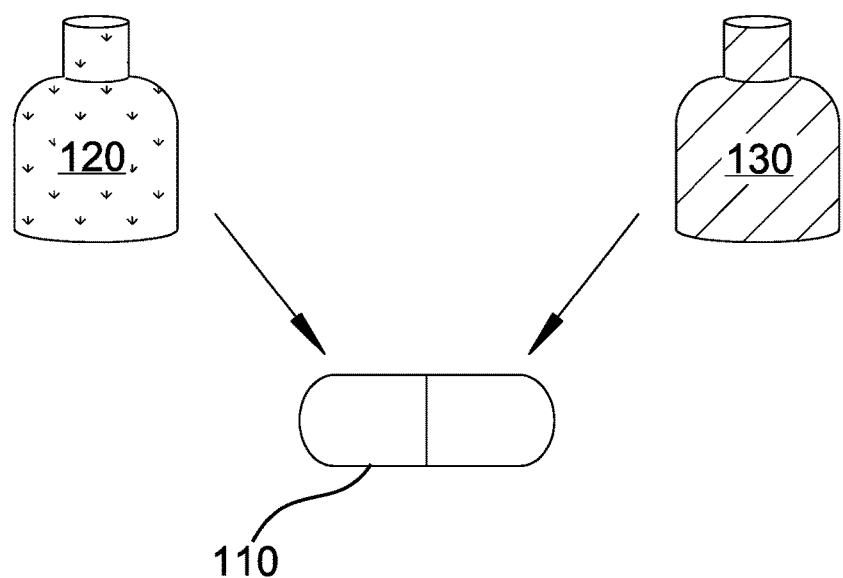
FIG. 1A illustrates two taggants prior to applying to a drug capsule.

Drug, as used herein, means any pharmacologically active agent or mixture of agents. Drug may also include an active ingredient in a health product, including a nutritional supplement. Drug may include one or more placebos.

Biological sample, as used herein, means urine, feces, whole blood, serum, plasma, cerebrospinal fluid, ascites, mucous, gastric gavage, saliva, breath, breast milk, or any combination thereof.

User, as used herein, means a patient, a participant in a medical study, or any individual who has consumed a drug composition which includes at least one taggant as described herein. The user may be animal or human.

Medical toilet, as used herein, means a device that may be used to collect one or more biological waste products of a user. This may include a traditional water toilet. However, medical toilet, as used herein, may mean any device which may be used to collect bodily waste according to the present disclosure and which may be equipped to analyze bodily waste according to the present disclosure.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose a method of applying taggants to or mixing taggants with drug compositions for later detection of the taggants. The method includes detection of the taggants in a biological sample obtained from the user who has consumed the drug composition and assessment of decay of the drug in the drug composition. In some embodiments, multiple taggants are used. In one embodiment, the first taggant includes multiple chemical molecules in a defined ratio. The ratio may be unique to a variety of details about the drug composition including manufacturer, drug, formulation, drug composition, manufacturing batch, dispensing pharmacy, prescribing healthcare provider, healthcare provider's institution, and prescribed user.

Taggants may be sprayed on pills, included as a powder or liquid ingredient in a pill or capsule or dispersed or dissolved in a liquid medication. The taggants may also be dusted on pills, adhered to pills and pills may be dipped in taggant solutions. In an example the taggants are mixed with the drug in powder form before pill or capsule formation so that the taggants are difficult to separate from the active ingredient in the drug composition. Each taggant may be colorized with a distinct visual color or combination of visual colors corresponding to its respective decay characteristics.

It may be useful to produce pills or other forms of medical formulations which include a placebo instead of an active drug molecule. This may be useful in conducting clinical studies. The disclosed method may be used to confirm that the study protocol was followed and that the patients received the correct pill or medical formulation. Alternatively, the method may be useful to keep those conducting the study blind to which study group a subject is assigned to. The subject's consumption of the drug or placebo may be confirmed after consuming the drug or placebo.

The chemicals included in the taggants may be sensitive to one or more of a variety of conditions. These may include light sensitivity, decay due to temperature sensitivity, decay due to moisture, and decay due to chemical degradation over time. Decay over time may include oxidation over time which may be a result of oxygen exposure. If the sensitivity to specific conditions and the corresponding decay rate of the taggant is the same or similar to that of the drug in the drug composition, the decay of the drug in the drug composition may be extrapolated to that of the taggants.

In an example, a first chemical is provided in concentration $C1$ and a second chemical is provided in concentration $C2$. The first and second chemicals are present in the drug composition in a ratio $C2/C1$ which represents taggant $T21$. A third chemical is provided in a concentration of $C3$ and at a ratio to the second chemical of $C3/C1$ which represents taggant $T31$. A user consumes the drug composition with the taggants and the amount of taggants excreted in the user's urine are measured. The reduced amounts of chemicals may be represented by $C1^*$, $C2^*$, and $C3^*$ which are present in ratios $C1^*/C2^*$ and $C3^*/C1^*$. The decay characteristics of each of the three chemicals is known and may be extrapolated to indicate the amount of drug in the drug composition that has decayed.

In another example, if the degradation rates of all taggants are different, with enough taggants, paths in a multidimensional space may be used to categorize the drug even in a decayed or partially decayed state. Taggants with different decay rates may reduce the number of possible distinct taggant ratios as one ratio may degrade into a different ratio, so that the second ratio is not useful. However, since the decay ratios describe a bounded trajectory in the multidimensional dimensional space, classification of the taggant aging status is possible based on the position in the multidimensional space of concentration ratios.

When a user consumes multiple drug molecules with associated taggants, multivariate techniques may be used to estimate the contributing fractions. Where co-consumption of drugs is indicated, taggant ratios of increased orthogonality may be used to improve multivariate discrimination.

In some embodiments, a plurality of taggants may have negligible or similar decay profiles. An additional taggant may be added that has a different decay profile to assist in extrapolating the decay profile of the taggants to that of the drug in the drug composition.

In some embodiments, taggants with qualitatively similar or identical and kinetically similar properties may be used. Even if the precise degradation rates differ, a mathematical relationship may be used to relate the degradation of one compound to another if the relative decay rates are known. In an example, there is a known half-life for decay of a drug due to age under nominal conditions. The detected decay of the taggant infers that the drug composition has been stored for a period of elapsed time. Consequently, by knowing the elapsed time and half-life of the drug composition, the amount of active drug remaining may be estimated.

In another example two taggants with different heat sensitivities are included in a drug composition. As one of skill in the art will understand, the reaction rate $k1$ of a molecule is assumed to be exponentially related to the temperature $T$ by an Arrhenius relationship $k1=A1^*\exp[-E1/(RT)]$, where $R$ converts temperature to energy units (gas constant), $A$ is frequency factor, and $E1$ is the activation energy. In this example, the decay of a drug in a drug composition that includes the two taggants is strongly dominated by high temperature excursions. By comparing the degradation fraction of two taggants with different energies it is possible to approximate the time at which the drug was at an elevated temperature and what that temperature was (under the assumption of decay is dominated by a single high temperature excursion or multiple equivalent high temperature excursions). We refer to the two taggants as taggants 1 and 2 and assume to decay independently of each other. The concentrations of taggants 1 and 2 (referred to as $C1$ and $C2$ respectively) detected in a biological sample and normalized to initial concentrations (or presented in a ratio with a highly stable taggant) may be expressed as follows $C1(t)=\exp(-k1^*t)$, $C2(t)=\exp(-k2^*t)$. The reaction rates are $k1=A1^*\exp[-E1/(RT)]$ and $k2=A2^*\exp(-E2/RT)$. Time may be eliminated from the equations to find a formula for temperature $T=(E2-E1)/(R^*\ln(\gamma))$, where $\gamma=A2^*\ln(C1)/(A1^*\ln(C2))$. Time may be calculated using the temperature and the exponential decay formula. Then, by knowing the time and the temperature, the decay of the drug may be estimated via its Arrhenius equation.

In some embodiments, the concentration of one or more of the taggants is approximately the same as the concentration of the drug in the drug composition. The concentration of the drug taggants, either individually or jointly, may exceed the concentration of the drug, or drugs, by approximately between 50 percent and 100 percent. This scenario assists in providing quantitative information about the amount of drug in the drug composition that enters or leaves the user's body in addition to its decay profile. Also, it may be useful that the entire drug composition consists of drug taggants in scenarios to designed to determine the consumption habits of the user and in scenarios where a drug placebo is used.

In some embodiments, the decay rate of the taggants (kinetic decay rate) in response to specific conditions is approximately the same as the drug in the drug composition. This scenario assists in providing quantitative information about the decay of the drug in the drug composition the user has consumed.

In some embodiments, the drug in the drug composition and at least one of the unique drug taggants possess qualitatively the same decay characteristic as well as kinetically the same decay characteristic. In this example, the decay of the at least one of the unique drug taggants may be directly extrapolated to decay of the drug in response to the environmental condition that triggers the shared decay characteristic.

In some examples, the drug composition may include a third unique drug taggant which is stable in the presence of a variety of environmental conditions. For example, the third unique drug composition may be stable in response to light, temperatures outside a range recommended for storage of the drug, oxygen exposure, moisture, and time. This third unique drug taggant may act as an internal control to correct for loss of taggant due to clearance by the user's body. In some examples, the third unique drug taggant may be cleared by the same biological system as the drug. In some examples, the third unique drug taggant may be cleared by the renal system, hepatic system, or a combination thereof.

In some embodiments, multiple taggants with different decay sensitivities may be applied to or mixed with the drug composition. For example, one taggant may spontaneously decay over time, one taggant may be sensitive to light exposure, and one taggant may be sensitive to temperatures outside a defined range. When this plurality of taggants is applied to or mixed with a drug composition, the history of the conditions to which the drug composition has been exposed may be determined.

The disclosed method may measure and report or record the detected spectrum or chemical dispersion. A processor may calculate the relative ratios of taggants. Based on the position in a multi-dimensional space of taggant ratios, the amount of decay in one or more axes (for example, age and exposure to heat and light) may be estimated. This calculation may be performed locally on the system or equivalently by a remote processor.

In some embodiments, the disclosed method may function as a drug consumption monitoring system. This system may include a user-identification system for correlating consumed drugs to users. The user-identification system may include methods for identifying users which include bioanalytics (for example, fingerprint, voice print, and electrocardiogram), user registration methods (for example, username and password), behavioral metrics, and combinations thereof.

The biological sample that is analyzed to identify or quantify one or more taggants may include one or more of the following: urine, feces, whole blood, serum, plasma, cerebrospinal fluid, ascites, mucous, gastric gavage, saliva, breath, and breast milk.

In some embodiments, the taggants are detected in the biological sample using one or more of the following analytical techniques: gas chromatography-mass spectrometry, liquid chromatography, capillary zone electrophoresis with UV absorbance, high performance liquid chromatography with UV absorbance, reverse-phase chromatography, fluorescence spectroscopy, high performance thin layer chromatography, UV spectroscopy, infrared spectroscopy, near IR spectroscopy, mid-IR spectroscopy, visible spectroscopy, nuclear magnetic resonance, ion mobility spectrometry, liquid chromatography-ion mobility spectroscopy, liquid chromatography-electrochemical detection, liquid chromatography-UV spectroscopy with a normal UV photodetector, thin layer chromatography, liquid chromatography, Raman spectroscopy, colorimetric assay, and mass spectrometry. In some embodiments, the taggants are detected in the biological sample using near IR spectroscopy. In some embodiments, the near IR spectroscopy analysis may be conducted using at least one excitation wavelength of between about 1 micron and about 2.5 microns. In some embodiments, spectroscopy analysis may be conducted using at least one excitation wavelength of between about 250 nm and about 800 nm. In some embodiments, the taggants may be measured using colorimetric chemical reactions which may be conducted on a color change chemistry strip.

In some embodiments, the analysis of the taggants may be conducted by an instrument that is within or connected to a medical toilet. The medical toilet may include a urine capture system and a urinalysis system.

The taggants may comprise of one or more of polyethylene glycol, copovidone, povidone, propylparaben, methyl paraben, acesulfame potassium, mannitol, sorbitol, xylitol, steviol glucuronide, sucralose, oleic acid, trans-anethole, 1,8-eucalyptol, limonene-2D, riboflavin, tartaric acid, salts of tartaric acid, linalool, and citronellol. Trans-anethole is a component of anise oil, 1,8-eucalyptol is a component of eucalyptus oil, and limonene-2D is a component of orange oil. Linalool is a component of coriander oil and citronellol is a component of rose oil or geranium oil. Consequently, the taggants may include anise oil, eucalyptus oil, orange oil, coriander oil, rose oil, and geranium oil.

In embodiments in which polyethylene glycol is included in the taggants, the polyethylene glycol may include polymers with an average molecular weight of between about 400 and about 2000. In some embodiments, the polyethylene glycol included in the taggants may include of one or more of the following average molecular weights: 400, 600, 800, 1000, 1500, and 2000. These relatively small average molecular weights are detectable in biological samples, including urine. However, unlike the larger molecular weight polyethylene glycol polymers, they do not act as laxatives.

In some embodiments in which povidone is included in the taggants, the povidone molecules may be polymers that include 25-mers, 30-mers, 90-mers or a combination thereof.

The disclosed method may be used to determine when the user consumed the drug composition. The drug composition may include at least two taggants. The at least two taggants may have known pharmacokinetic properties which may be detectably different from each other. The amount of the taggants measured in a user's bodily waste, particularly over time, may provide an estimate of the time the taggants, and thus the drug, were consumed. In some embodiments, the taggants may be detectable by near infrared spectroscopy. In some embodiments, the taggants may be cleared by the same biological system as the drug in the drug composition. For example, the renal or hepatic systems may clear both the drug and at least one of the taggants. The at least one taggant in the biological sample may, therefore, be used to normalize for impaired liver or kidney function which may impact drug metabolism.

In another example the pharmacokinetic rates of taggant molecules may be different, so the measured ratios of taggants trace a path through a multidimensional taggant ratio space, similar to the case of aging drug compositions, except in this case the ratios are indicative of time since consumption. For instance, the amount of a taggant detected in urine may quickly decrease due to metabolic processing. Urine received soon after consumption may have a higher concentration than urine received a long time after consumption. In contrast, the amount of another taggant measured in the user's urine may decrease more slowly over time. A similar result is achieved for different uptake and elimination rates.

Referring now to the drawings, FIG. 1A illustrate drug capsule 110 which includes a drug composition. Drug capsule 110 has not yet been exposed to a taggant. In this embodiment, two chemicals, chemical 120 and chemical 130 are shown and will be sprayed on the surface of a different half of drug capsule 110 according to the arrows.

Figure 1B:
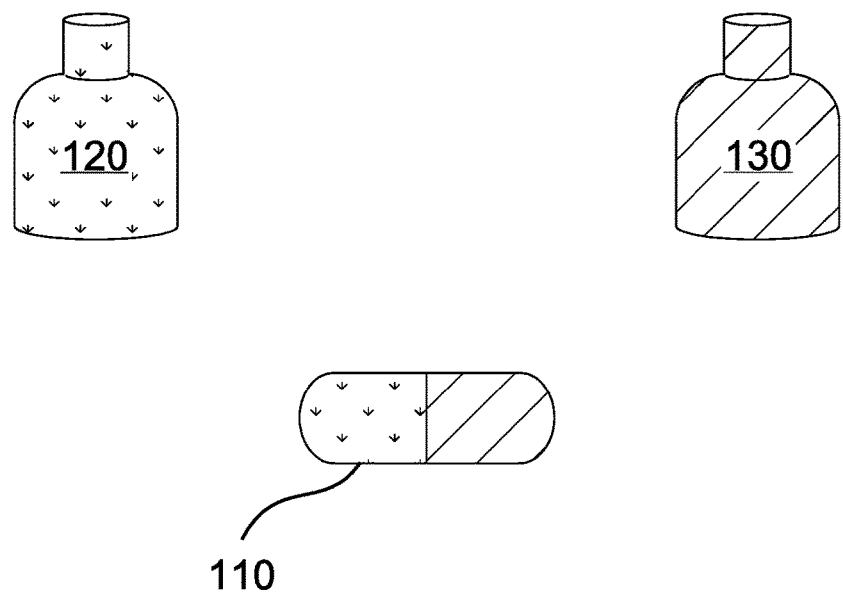
FIG. 1B illustrates the drug capsule of FIG. 1A after the two taggants have been applied.

FIG. 1B shows drug capsule 110 after chemicals 120 and 130 have been sprayed on its surface. The different shadings on drug capsule 110 correlate with the shadings on the bottles of chemicals 120 and 130.

Figure 2:
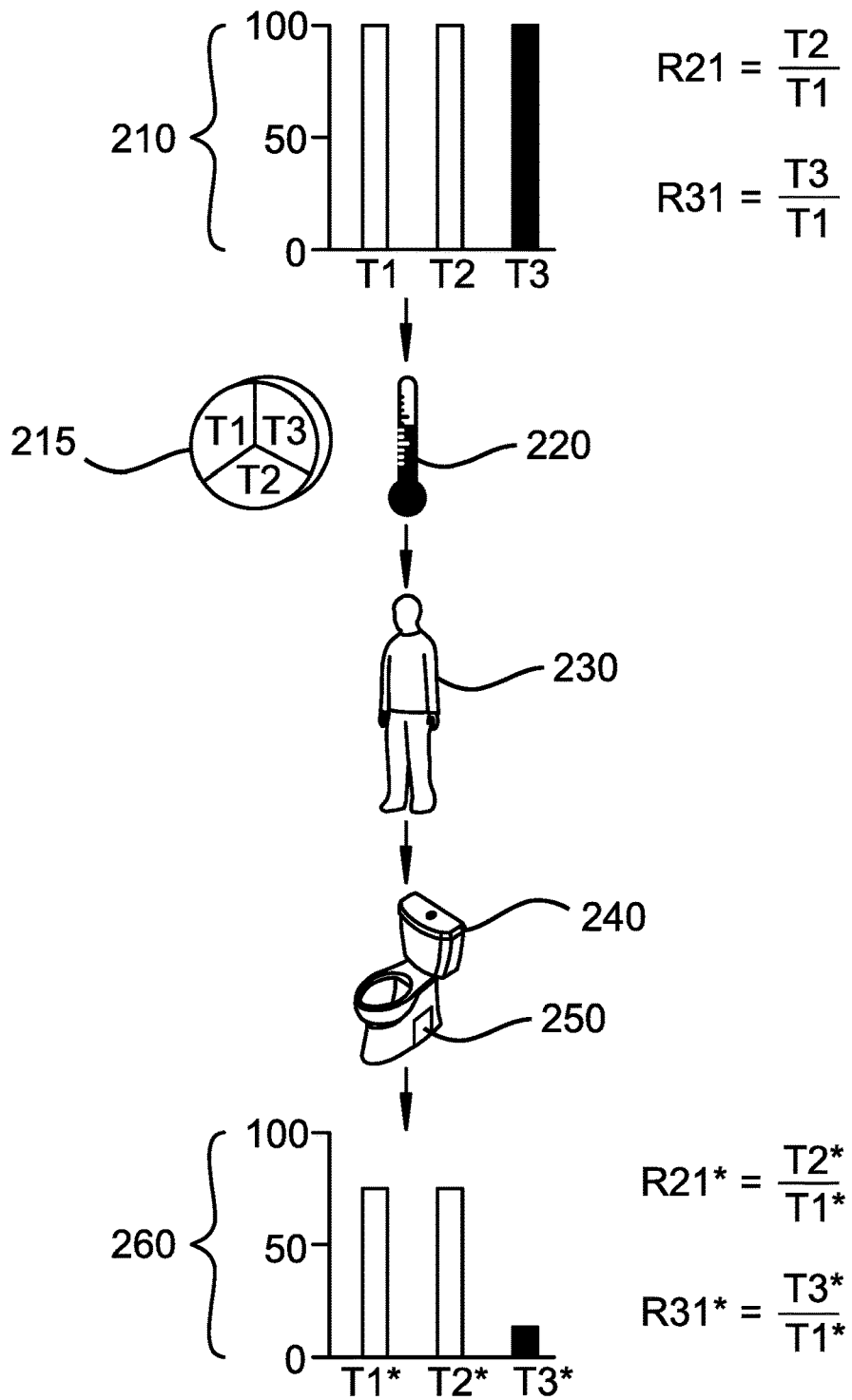
FIG. 2 illustrates a method of using three taggants which have been applied to a medication in defined ratios and consumed by a user to assess drug degradation due to excessive heat.

FIG. 2 illustrates a method of using three chemicals as taggants for a drug composition. The three chemicals are T1, T2, and T3 and their original amounts are shown as 100% in bar graph 210. To the right of bar graph 210, the original ratios of chemicals T1, T2, and T3 are shown. The first ratio, R21, is the ratio of T2 to T1. The second ratio, R31, is the ratio of T3 to T1. R21 and R31 represent two taggants. They are unique to other taggants because of the chemicals and because of their relative ratios. The three chemicals have been applied to a drug composition, illustrated as tablet 215 in ratios R21 and R31. In this example, the decay rates of T1 and T2 in response to heat are negligible relative to T3. At some point, tablet 215 is exposed to temperature 220, illustrated in FIG. 2 as a thermometer. Temperature 220 is above the recommended storage temperature for tablet 215 because the drug in tablet 215 is heat sensitive. Consequently, at least one chemical which is similarly heat sensitive is included in the taggants. T3 is especially heat sensitive so failure to detect the original amount of T3 in a user's biological waste indicates heat exposure.

User 230 consumes tablet 215 and then urinates in medical toilet 240. Medical toilet 240 includes spectrophotometer 250 which analyses the urine from user 230 using wavelengths in the near IR range. The percentages of the original amounts of T1, T2, and T3 that were applied to tablet 215 at the time of manufacture are measured in the near IR spectroscopy analysis and are found to be reduced. The altered T1, T2, and T3 are presented in bar graph 260 as T1*, T2*, and T3* respectively. The original ratios R21 and R31 are also altered and presented at R21* and R31* respectively. This analysis indicates that the drug in tablet 215 has been exposed to excessive heat and tablet 215 may have contained less active drug at the time user 230 consumed than it did at the time of manufacture.

Figure 3:
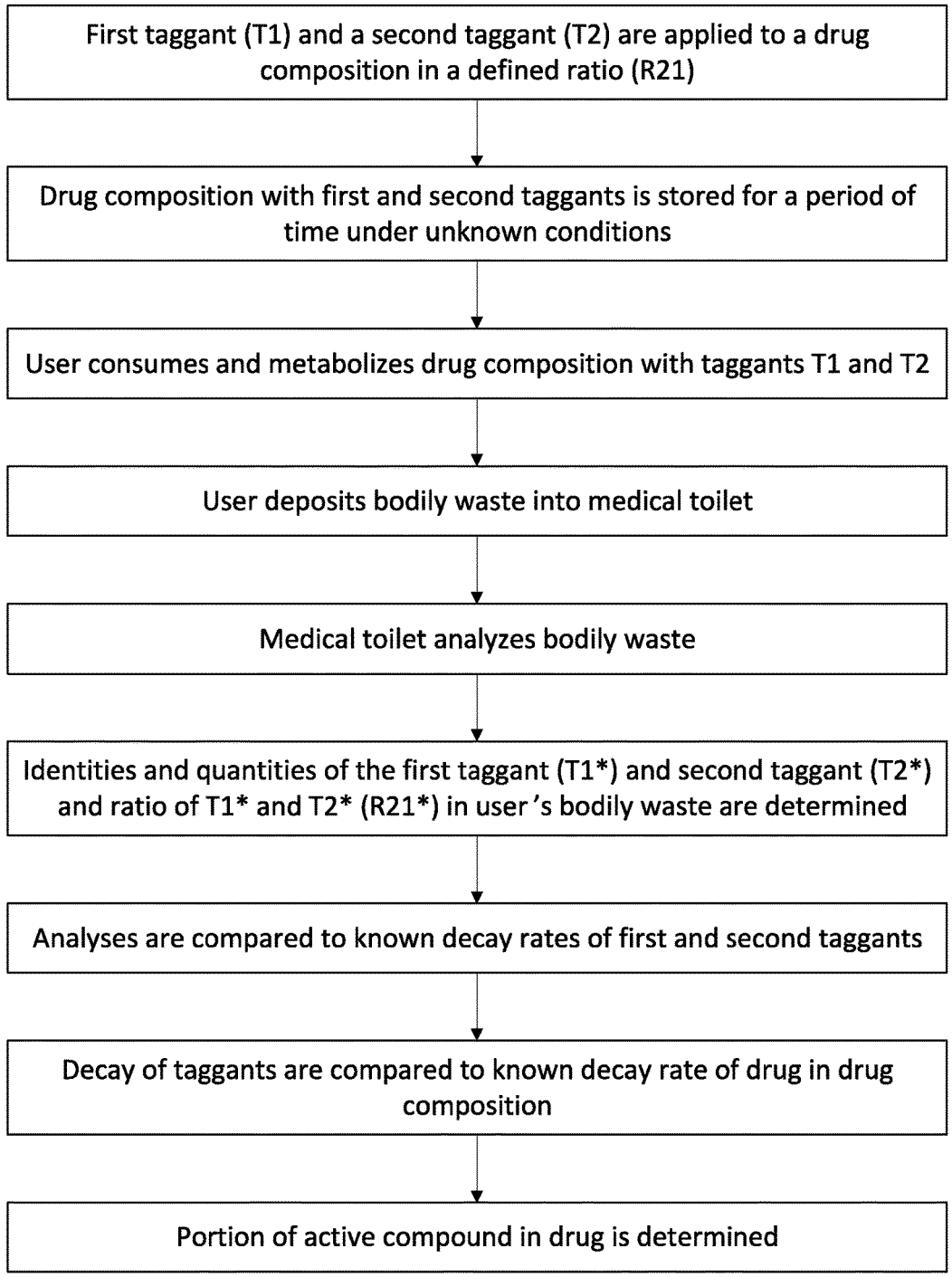
FIG. 3 provides a flow chart which includes steps which may be used in performing an embodiment of a method of using the disclosed drug tagging system to assess drug degradation over time.

FIG. 3 is a flow chart illustrating a series of steps which may be performed to assess the length of time a drug has been stored prior to consumption. In this embodiment, there are two taggants, T1 and T2 which have been applied to a drug composition in defined ratio R21. The drug composition with the two taggants is stored for a period of time under unknown conditions. The drug composition has a shelf life beyond which the drug becomes less active. The drug may also be sensitive to other conditions, for example, light and extreme temperature. A user consumes the drug composition along with the two taggants then deposits bodily waste into a medical toilet. The medical toilet includes a spectrometer which analyzes the bodily waste using near IR spectroscopy.

The near IR spectroscopy analysis identifies and quantifies the two taggants. The amount of the taggants identified in the bodily waste is reduced relative to the amount applied to the drug composition. The reduced amounts of T1 and T2 are referred to as T1* and T2* and have been found in the bodily waste in altered ratio R21*. The decays of the two taggants are compared to known decay rate of the drug in the drug composition in response to different environmental and temporal conditions. The portion of active drug in the drug composition at the time the user consumed the drug composition is then determined FIG. 4 provides a table which lists examples of chemical entities which may be used in taggants according to the disclosure along with their chemical structures. These include polyethylene glycol, ethylene-vinyl acetate, copovidone, povidone, propylparaben, sucralose, methyl paraben, acesulfame potassium, mannitol, sorbitol, and xylitol. The compounds in the table of FIG. 1 are relatively stable over time and various environmental conditions.

Figure 5:
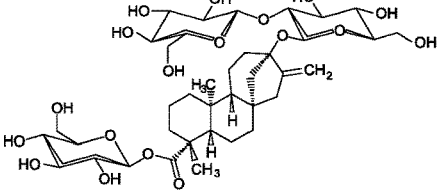
FIG. 5 is a table showing the names and chemical structures of examples of molecules which are less stable and which may be used in taggants according to the disclosure.
Figure 5:
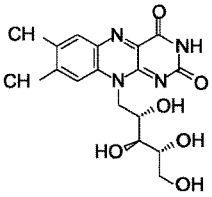
Figure 5:
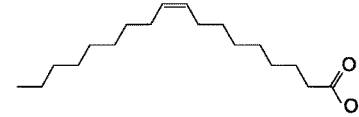
Figure 5:
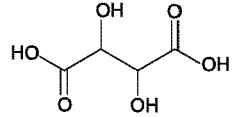
Figure 5:
Figure 5:
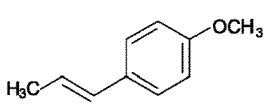
Figure 5:
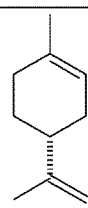
Figure 5:
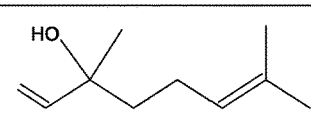
Figure 5:
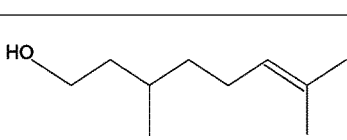

FIG. 5 provides a table which lists examples of chemical entities which may be used in taggants according to the disclosure along with their chemical structures. These include steviol glucuronide, sucralose, oleic acid, trans-anethole, 1,8-eucalyptol, limonene-2D, riboflavin, tartaric acid, salts of tartaric acid, linalool, and citronellol. Trans-anethole is a component of anise oil, 1,8-eucalyptol is a component of eucalyptus oil, and limonene-2D is a component of orange oil. Linalool is a component of coriander oil and citronellol is a component of rose oil or geranium oil. Accordingly, anise oil, eucalyptus oil, orange oil, coriander oil, rose oil, and geranium oil may be used in taggants. These chemical entities are relatively unstable over time so may be used to assess the amount of time that has passed after applying the tag to the drug composition or nutritional composition.

Figure 6:
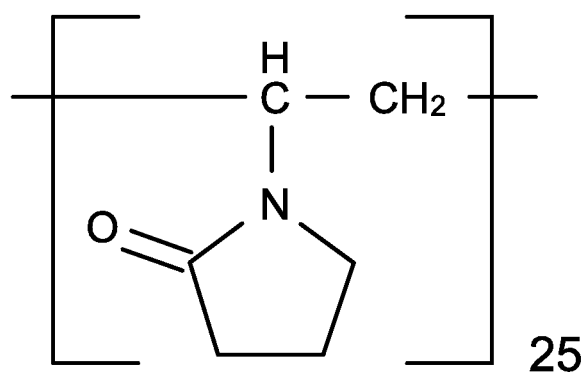
FIG. 6 shows three variations of povidone which may be used in taggants according to the disclosure.
Figure 6:
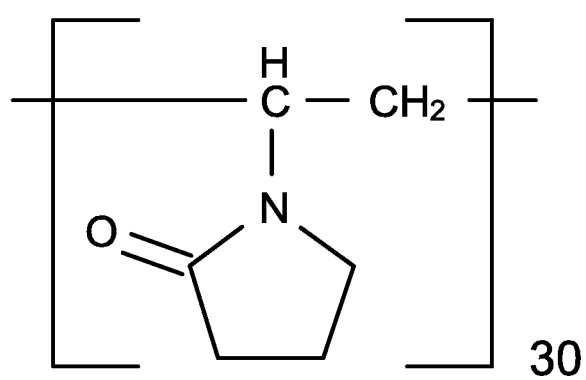
Figure 6:
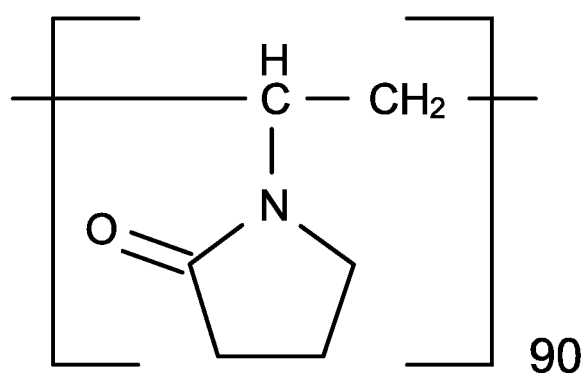

FIG. 6 shows three forms of povidone which may be used in taggants according to the disclosure. These include polymers of varying sizes including a 25-mer, a 30-mer, and a 90-mer.

FIG. 7 provides a table which lists examples of polyethylene glycols of varying average molecular weights. These include PEG 400, PEG 600, PEG 800, PEG 1000, PEG 1500, and PEG 2000. Polyethylene glycol is a polymer made of varying numbers of monomers and each polyethylene glycol solution may be comprised of a range of molecular weights, depending on the number of monomers in the polymers, with an average molecular weight.

Figure 8:
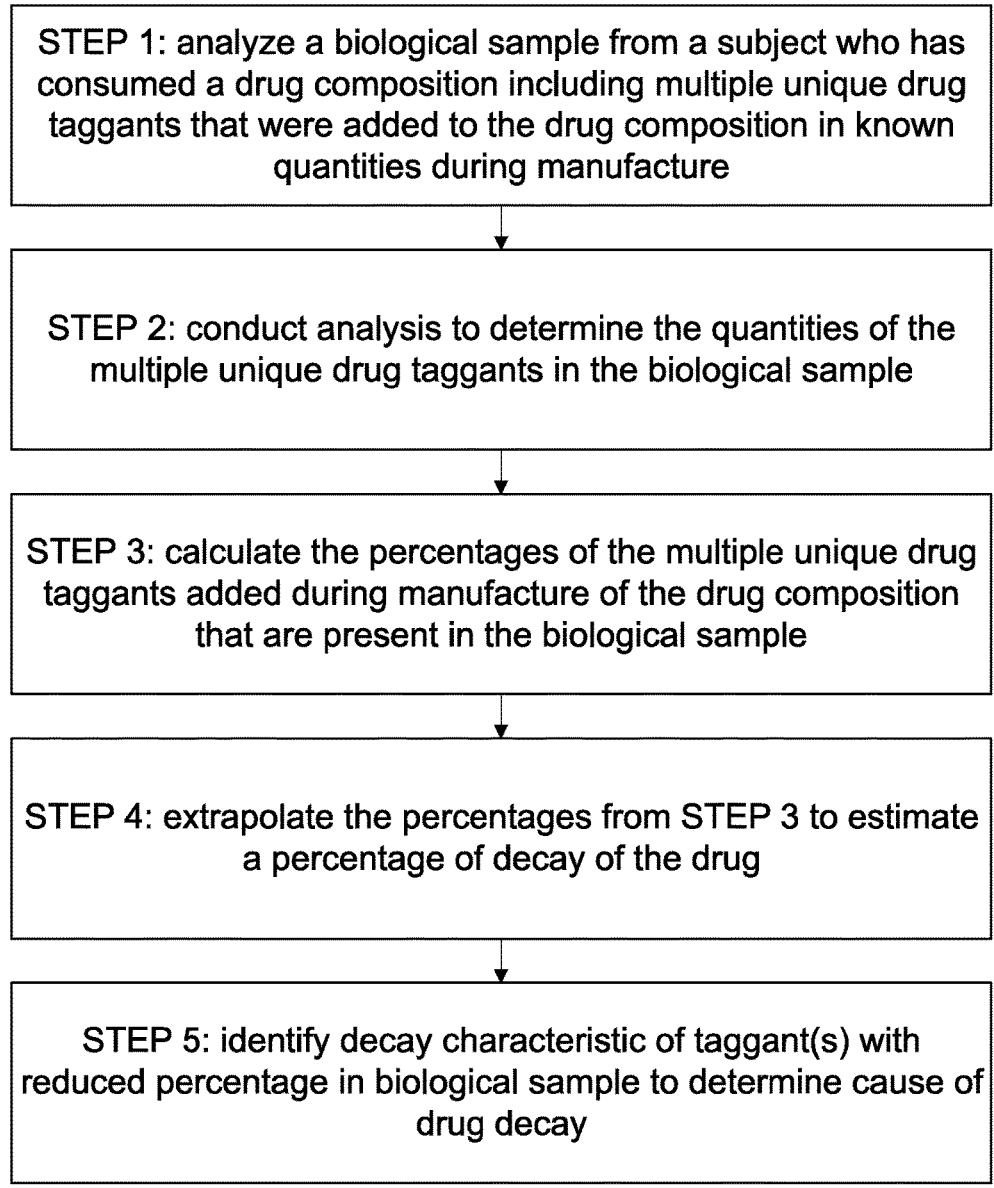
FIG. 8 provides a flow chart which includes steps which may be used in performing an embodiment of a method of using the disclosed drug tagging system to determine the cause of drug decay in a consumed drug composition.

FIG. 8 shows a flow chart which includes steps which may be used to determine the percentage of decay of a consumed drug and the environmental condition that caused the decay prior to consumption. In this example, the user is a study subject. Also, in this example, each of the multiple unique drug taggants has a different decay characteristic which is one of the decay characteristics the drug in the drug composition possesses.

Step 1 shown in FIG. 8 is to analyze a biological sample from a subject who has consumed a drug composition. The drug composition included multiple unique drug taggants which were added to the drug composition before the user consumed the drug composition. In this example, the multiple unique taggants were added to the drug composition in known quantities during manufacture of the drug composition. Step 2 includes an analysis of the biological sample to determine the quantities of the multiple unique drug taggants. Now, the identities and the quantities of the drug taggants in the biological sample are known as well as the quantities of the unique drug taggants which were added to the drug composition during manufacture.

In Step 3, the percentage of each unique drug taggant detected in the biological sample is calculated. For example, the percentage may be calculated for each taggant according to the following formula:

100*(taggant in biological sample)/(taggant added during manufacture).

In Step 4, the percentage of drug decay is extrapolated from the percentage of decay of the taggants as calculated in Step 3. Note that this is possible because the taggants collectively have the same decay characteristics as the drug in the drug composition.

In Step 5, the type of environmental conditions that cause the drug to decay are identified by noting the decay sensitivities of the taggants with reduced quantities in the biological sample.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A method of detecting drug taggants in biological sample to assess decay of a drug in a drug composition comprising the steps of:
   a) detecting a signal produced by a first and a second drug taggant in the biological sample which was collected from a user who has consumed at least one drug composition,
      i. wherein each of the at least one drug composition comprises the following, each in a known quantity and in a first ratio, at the time of manufacture of the drug composition: at least one drug or placebo, and the first and the second drug taggants,
      ii. wherein the first drug taggant comprises a first decay characteristic and the second drug taggant comprises a second decay characteristic,
      iii. wherein the first decay characteristic is detectably different from the second decay characteristic, and
      iv. wherein the at least one drug or placebo comprises the first and the second decay characteristics;
      v. wherein the first decay characteristic and the second decay characteristic are independently selected from the following: decay due to light sensitivity, decay due to temperature sensitivity, and decay due to moisture;
      vi. wherein the first decay characteristic is a qualitatively different characteristic than the second decay characteristic; and
      vii. wherein the first decay characteristic is qualitatively the same as a decay characteristic possessed by the drug, and wherein the first decay characteristic is kinetically approximately the same as the decay characteristic possessed by the drug; and
      viii. wherein the first drug taggant and the second drug taggant are independently selected from the following: polyethylene glycol, copovidone, povidone, propyl paraben, methyl paraben, acesulfame potassium, mannitol, sorbitol, xylitol, steviol glucuronide, sucralose, oleic acid, trans-anethole, 1,8-eucalyptol, limonene-2D, riboflavin, tartaric acid, salts of tartaric acid, linalool, and citronellol; and
   b) calculating a second ratio of the first and the second drug taggants present in the biological sample;
   c) identifying one or more decay characteristics which caused the decay of the drug; and
   d) extrapolating a difference between the first ratio and the second ratio to determine a fraction of decayed drug.

2. The method of claim 1, wherein the at least one drug composition comprises a placebo.

3. The method of claim 2, wherein the first ratio is indicative of one of the following: drug composition manufacturer, at least one drug, drug composition, manufacturing batch, dispensing pharmacy, prescribing healthcare provider, healthcare provider's institution, and prescribed user.

4. The method of claim 1, wherein either the first taggant or the second taggant consists of polyethylene glycol, and wherein the polyethylene glycol comprises polymers of one or more of the following average molecular weights: 400, 600, 800, 1000, 1500, and 2000.

5. The method of claim 1, wherein either the first drug taggant, the second drug taggant, or both the first and second drug taggants consist of polyethylene glycol, and wherein the polyethylene glycol comprises polymers with an average molecular weight of between about 400 and about 2000.

6. The method of claim 1, wherein either the first drug taggant, the second drug taggant, or both the first and second drug taggants consists of povidone molecules, and wherein the povidone molecules consist of one or more of the following number of monomers: 25, 30, and 90.

7. The method of claim 1, wherein the biological sample comprises one or more of the following: urine, feces, whole blood, serum, plasma, cerebrospinal fluid, ascites, mucous, gastric gavage, breath, saliva, breath, and breast milk.

8. The method of claim 1, wherein the first taggant and the second taggant are detectable in the biological sample using one or more of the following analytical techniques: gas chromatography-mass spectrometry, liquid chromatography, capillary zone electrophoresis with UV absorbance, high performance liquid chromatography with UV absorbance, reverse-phase chromatography, fluorescence spectroscopy, high performance thin layer chromatography, UV spectroscopy, infrared spectroscopy, near IR spectroscopy, mid-IR spectroscopy, visible spectroscopy, nuclear magnetic resonance, ion mobility spectrometry, liquid chromatography-ion mobility spectroscopy, liquid chromatography-electrochemical detection, liquid chromatography-UV spectroscopy with a normal UV photodetector, thin layer chromatography, liquid chromatography, Raman spectroscopy, colorimetric assay, and mass spectrometry.

9. The method of claim 8, wherein the analytical technique is performed by an instrument connected to a medical toilet.

10. The method of claim 1, wherein a concentration of the first drug taggant, a concentration of the second drug taggant, or the concentration of both the first and the second drug taggants in the drug composition at the time of manufacture of the drug composition is approximately the same as a concentration of the drug.

11. The method of claim 1, wherein the first decay characteristic, the second decay characteristic, or both the first and the second decay characteristics are qualitatively the same as a decay characteristic of the drug.

12. The method of claim 1, which further includes a third drug taggant, wherein the third drug taggant is stable in response to light, temperatures outside a range recommended for storage of the drug, oxygen exposure, moisture, and time relative to the first and second drug taggants.

13. The method of claim 12, wherein the third drug taggant is cleared by the same biological system as the drug.

14. The method of claim 1, wherein the concentration of the drug taggants, either individually or jointly, exceed the concentration of the drug, or drugs, by approximately between 50 percent and 100 percent.

* * * * *